(12) United States Patent
Inaba

(10) Patent No.: US 7,020,919 B2
(45) Date of Patent: Apr. 4, 2006

(54) PILLOW

(75) Inventor: Yoshisada Inaba, Osaka (JP)

(73) Assignee: Kabushiki Kaisha Shinsei, Tenri (JP)

( * ) Notice: Subject to any disclaimer, the term of this patent is extended or adjusted under 35 U.S.C. 154(b) by 0 days.

(21) Appl. No.: 10/901,022

(22) Filed: Jul. 28, 2004

(65) Prior Publication Data

US 2006/0021147 A1     Feb. 2, 2006

(51) Int. Cl.
*A47G 9/00* (2006.01)

(52) U.S. Cl. .................................. 5/638; 5/641; 5/643

(58) Field of Classification Search .................... 5/638, 5/652.1, 643, 636, 640, 641, 951
See application file for complete search history.

(56) References Cited

U.S. PATENT DOCUMENTS 1,274,595 A * 8/1918 Ranz .............................. 5/636
3,258,790 A * 7/1966 Maru ............................. 5/636
6,763,538 B1 * 7/2004 Tsai .............................. 5/638

FOREIGN PATENT DOCUMENTS

| JP | 11-56558 | 3/1999 |
| JP | 11-266985 | 10/1999 |
| JP | 2000-60704 | 2/2000 |

* cited by examiner

*Primary Examiner*—Alexander Grosz
(74) *Attorney, Agent, or Firm*—Osha Liang LLP

(57) ABSTRACT

A pillow of an appropriate height, resiliency, and hardness, which is light in weight and excellent in strength and does not impose too much stress on a user's head and neck while enhancing air permeability and heat dispersion properties, provides good comfort to the user. The pillow 1 includes a pillow body 10 having a head-supporting section 11 for supporting the user's head and a neck-supporting section 12 for supporting the neck, and frame bodies 20A and 20B disposed at both sides of the pillow body 10 to support it. The pillow body 10 is a woven article of resin long elements and the neck-supporting section 12 is harder than the head-supporting section 11.

11 Claims, 10 Drawing Sheets

PILLOW

BACKGROUND

This invention relates to a resin-made pillow.

Pillows with various functions have been suggested.

For example, Japanese Patent Laid-Open Publication No. H11-56558 suggests a pillow, easily manufactured at low cost, comprising an interior member formed to a specified height by laminating a plurality of layers of slab urethane foam and an exterior member made from slab urethane foam wrapped around the periphery of the interior member.

Japanese Patent Laid-Open Publication No. H11-266985 suggests an ergonomic pillow preventing harmful stresses on the human body when lying on one's back or on one's side. This pillow comprises a head-supporting concave section, at the center of its upper surface, for stably supporting the back of a user's head when lying on his back, and a back-of-the-neck-supporting section, in front of the head-supporting concave section, for comfortably and desirably supporting the back of the user's neck. The pillow further comprises, at the sides of the back-of-the neck supporting section, sides-of-neck-supporting convex sections projecting out from the upper surface for supporting the left and right sides of the neck when the user is lying on his side, and shoulder-inserting concave sections at the front surface below the respective sides-of-neck-supporting convex sections.

Japanese Patent Laid-Open Publication No. 2000-60704 suggests a pillow enabling to adjust hardness and thickness of the pillow according to the user's preference. This pillow has a structure in which a plurality of cushions respectively containing fillings are piled up in a selectable piling order and contained in a pillow case. At least one of these cushions has a filling that exhibits a transformation ratio different from that of the fillings in the other cushions.

These conventional pillows have cushion materials contained therein and none of them has a structure in which resin-made long elements are woven into a pillow body as in the case of the present invention. It is desired to make improvements to these conventional pillows with regard to air permeability and heat dispersion properties.

SUMMARY

It is an object of this invention to provide a pillow of an appropriate height, resiliency, and hardness, which is light in weight and excellent in strength and does not impose too much stress on a user's head and neck while enhancing air permeability and heat dispersion properties, hence providing good comfort to the user.

In order to achieve the object, this invention provides a pillow comprising: a pair of frame bodies oppositely disposed and spaced apart from each other; and a pillow body disposed to surround the peripheries of the frame bodies, wherein the pillow body is a woven article of long elements and has a head-supporting section for supporting a user's head and a neck-supporting section for supporting the user's neck, and the neck-supporting section is made harder than the head-supporting section.

The pillow having such structure has the neck-supporting section that is made harder than the head-supporting section. Accordingly, when the user uses the pillow, the head-supporting section sinks gradually and naturally due to the weight of the head and the user will be in a state where the head is kept at a low position while the neck remains in the same position. Therefore, compared to other pillows, the pillow improves the condition of the respiratory organs and expands the respiratory airway, thus preventing snoring. The pillow can be preferably used by people with apnea syndrome. Moreover, the pillow is effective in solving insomnia and promoting one's health by guaranteeing excellent comfort while sleeping.

Moreover, the pillow has an appropriate height, resiliency, and hardness and does not impose unreasonable stress on the user's head and neck. Since the pillow body is a woven article of long elements, the pillow can enhance air permeability and heat dispersion properties and is lightweight and excellent in strength.

The long elements can be made from materials predominantly composed of resin.

The woven article can be arranged to surround the peripheries of the frame bodies.

The woven article comprises a weft extending from one of the body frame to the other body frame and a warp extending in a substantially vertical direction to the weft, and the weft arranged in the neck-supporting section may have a cross section, which is in a vertical direction in relation to the longitudinal direction of the weft, larger than that of the weft arranged in the head-supporting section.

The weft arranged in the neck-supporting section may have a structure harder than that of the weft arranged in the head-supporting section.

The weft arranged in the neck-supporting section may be of a different color from that of the weft arranged in the head-supporting section, so that the user can easily notice the correct orientation of the pillow when using it.

The long elements may be composed of nylon resin as its main component. Because nylon resin has excellent water absorbency, it is effective in absorbing heat and lowering the temperature of the head and the neck. Accordingly, in addition to the aforementioned advantages, the pillow can provide a further enhanced comfort to the user. The nylon resin-made pillow has another advantageous characteristic that its head-supporting section naturally sinks, when the user puts his head on the pillow, due to the weight of the head. Hence, the user can maintain an optimal state where the neck remains in the same position but the head is kept at a low position.

The respective frame bodies are nearly oval in shape when viewed from above and may have reinforcing members along its curved portions. According to this invention, one of the frame bodies of the pillow may be coupled to the other frame body by a supporting rod. As a result, the pillow will have still another advantage of enhancing the strength of the pillow.

At least either one of the warp and the weft can have a cross section in a substantially crescent form, substantially vertical to the longitudinal direction thereof.

The pillow according to this invention allows an optional article to be arranged in a space formed by the frame bodies and the pillow body. Examples of the optional article include fragrant materials, audio-generating devices, herbs and the like.

For example, in the case where a fragrant material is arranged in the space formed by the frame bodies and the pillow body, an aromatherapy effect can be obtained during the use of the pillow. In case of arranging a audio-generating device in the space, the user can listen to his favorite music, stories, or broadcasting stations while using the pillow. In case of placing herbs in the space, the user can promote his health by using the pillow.

There is no particular limitation to the audio-generating device and any device is applicable as long as it generates sounds, for example, a radio, tape recorder, MD player, CD player, music box, or a speaker that can be connected to an exterior sound source.

DETAILED DESCRIPTION OF DRAWING

Figure 1:
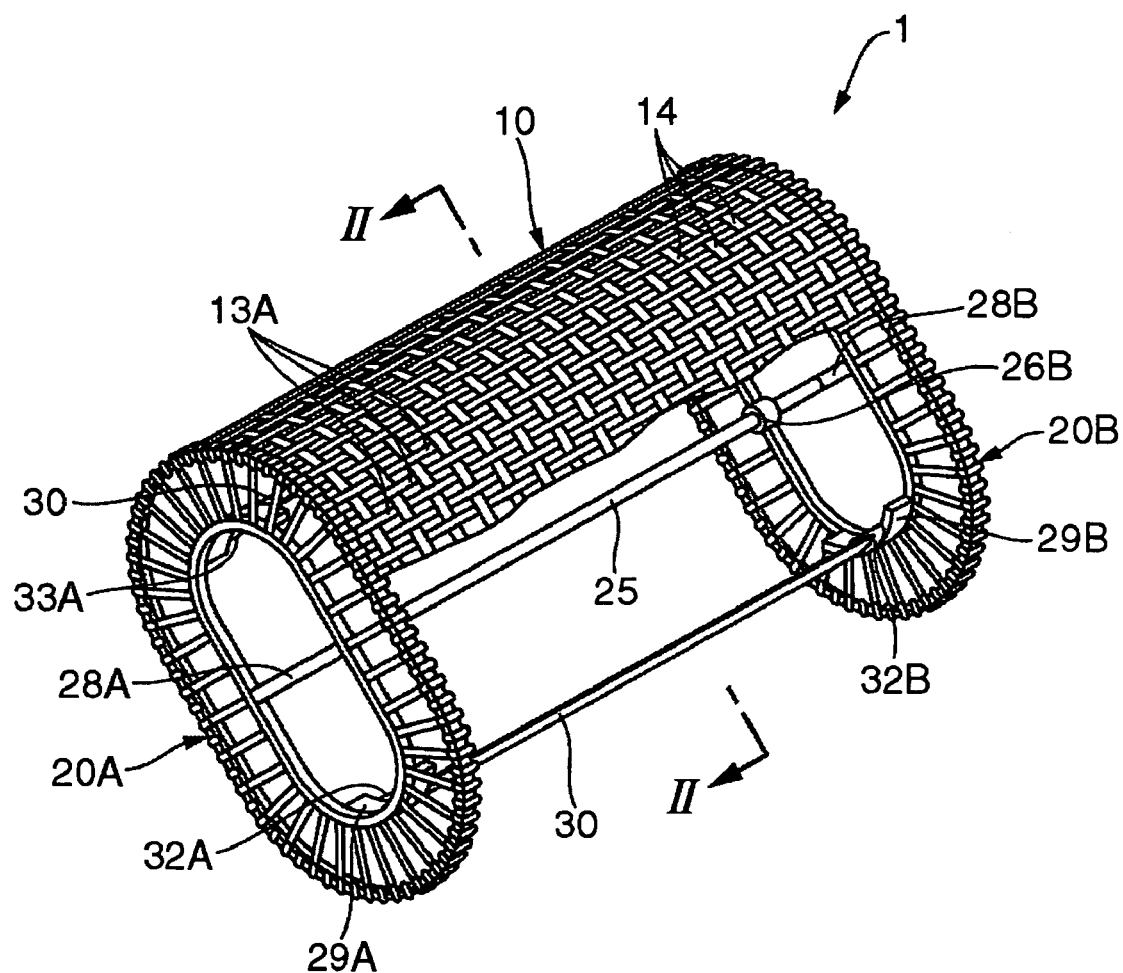
FIG. 1 is a perspective view of a pillow (partially omitted) according to an embodiment of this invention, some parts being cut away.
Figure 10A:
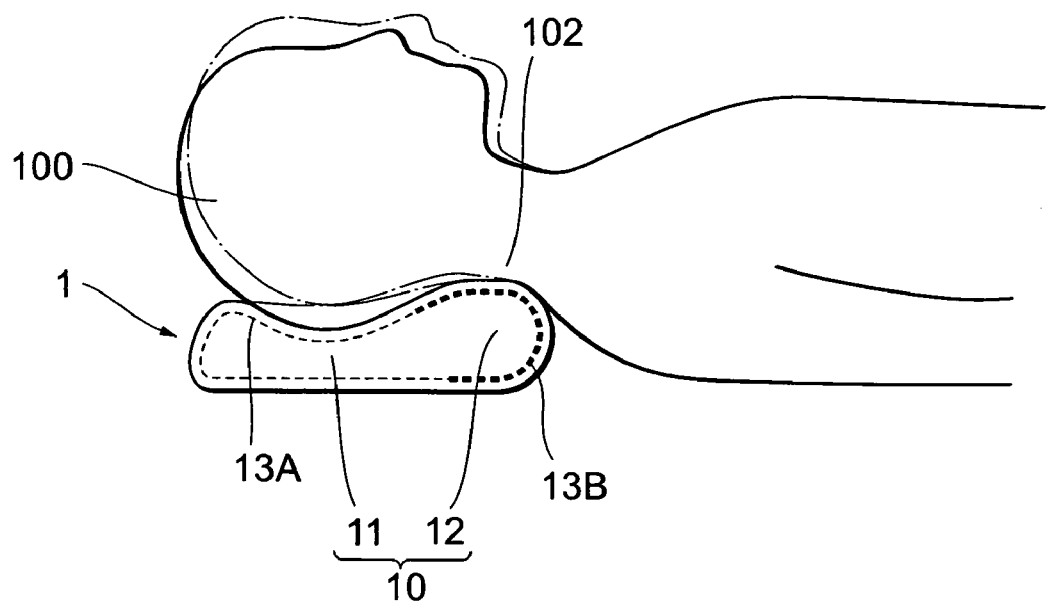
Figure 10B:
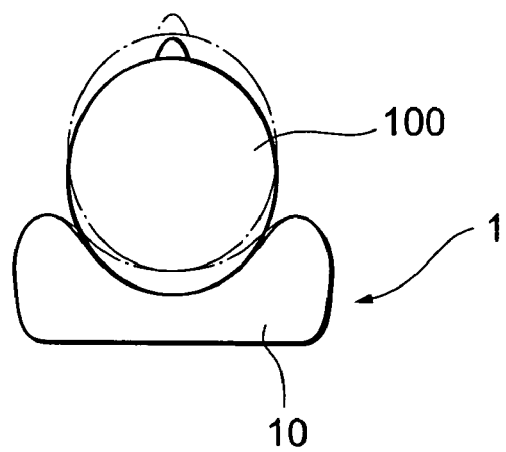

FIG. 10 (A) and (B) show the pillow in FIG. 1 in use.

DETAILED DESCRIPTION

A pillow according to a preferable embodiment of this invention will be explained with reference to drawings. The embodiment hereinafter described is for exemplifying an example of this invention and is not be intended to limit the scope of this invention to this embodiment. So as long as the gist hereof is not deviated, this invention may be worked in various forms and manners.

Figure 2:
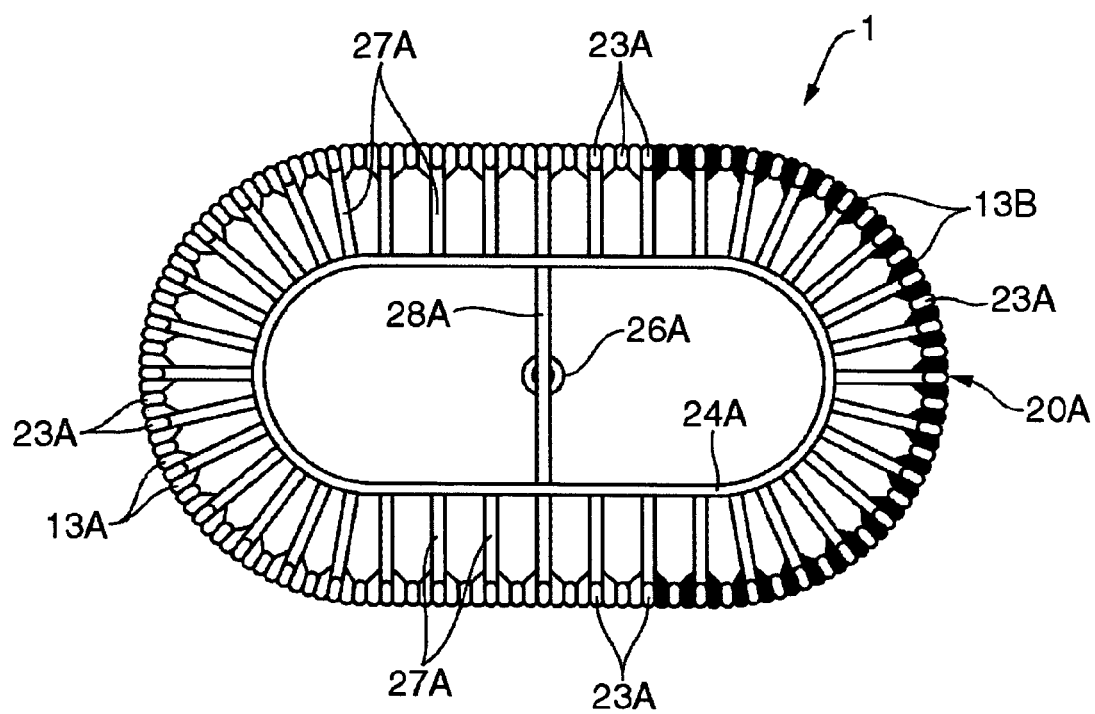
FIG. 2 is a side view of the pillow in FIG. 1 (thick wefts are indicated in black and thin wefts in white).
Figure 3:
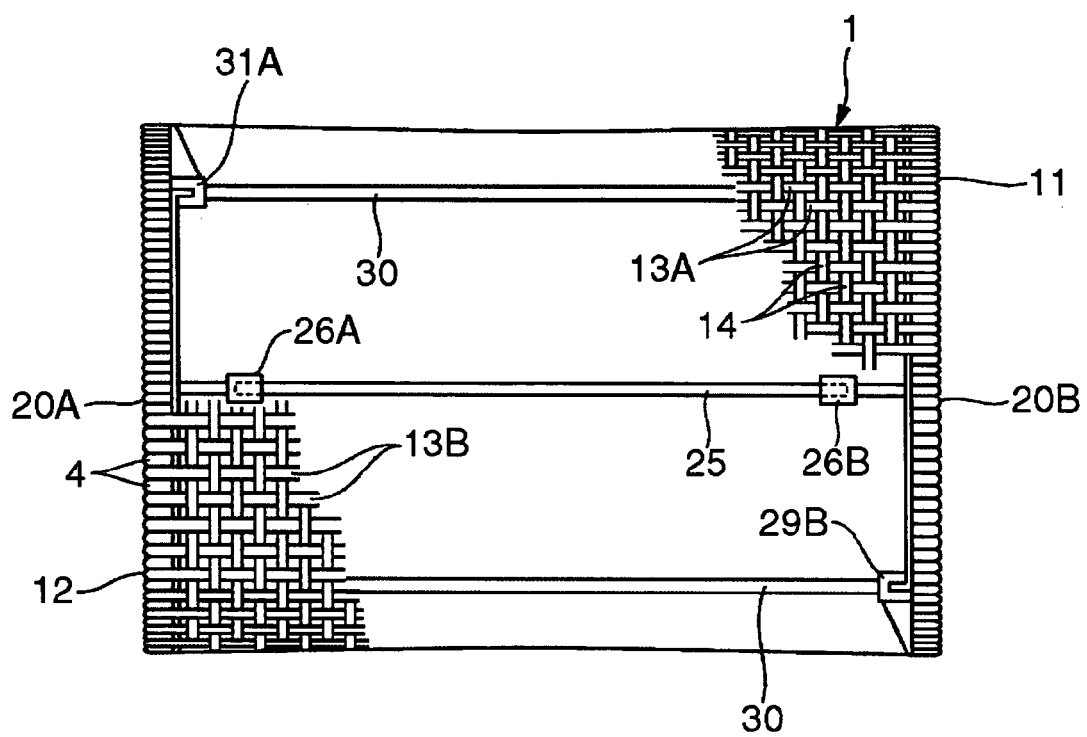
FIG. 3 is a plan view of the pillow in FIG. 1 (partially omitted).
Figure 4:
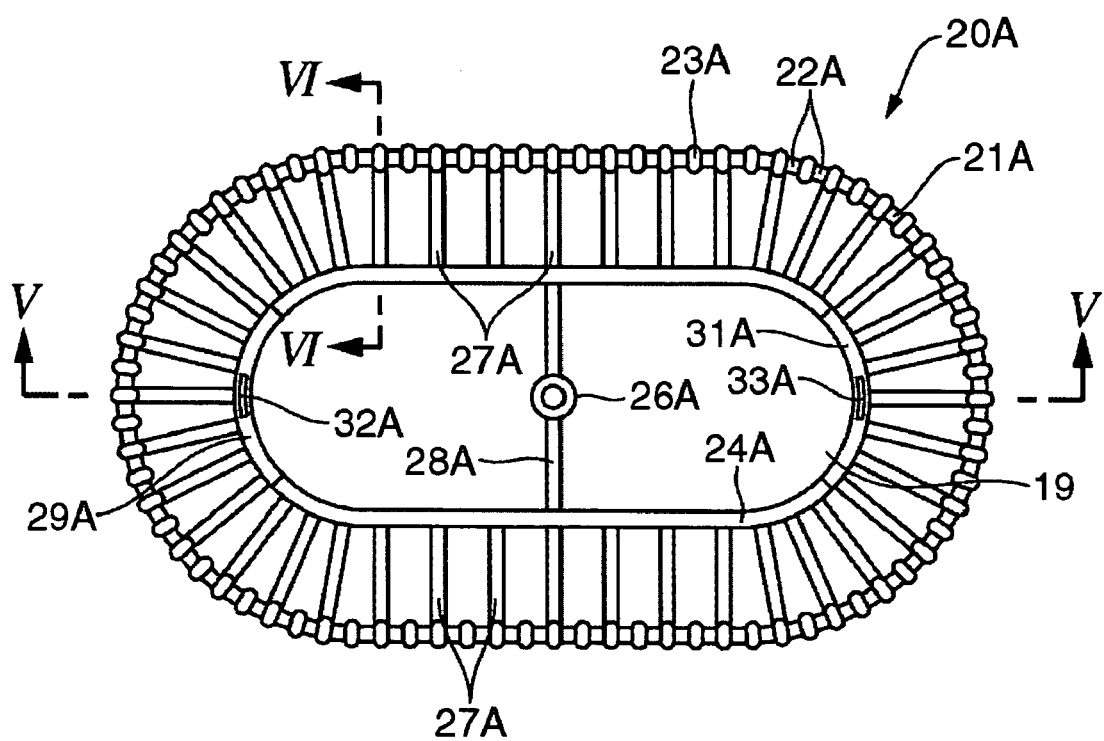
FIG. 4 is a sectional view of a frame body taken along line II—II in FIG. 1.
Figure 5:
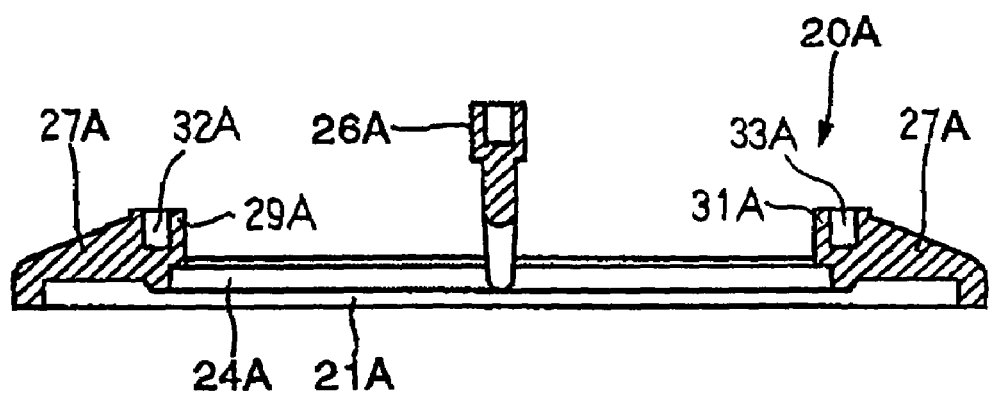
FIG. 5 is a sectional view taken along line V—V in FIG. 4.
Figure 6:
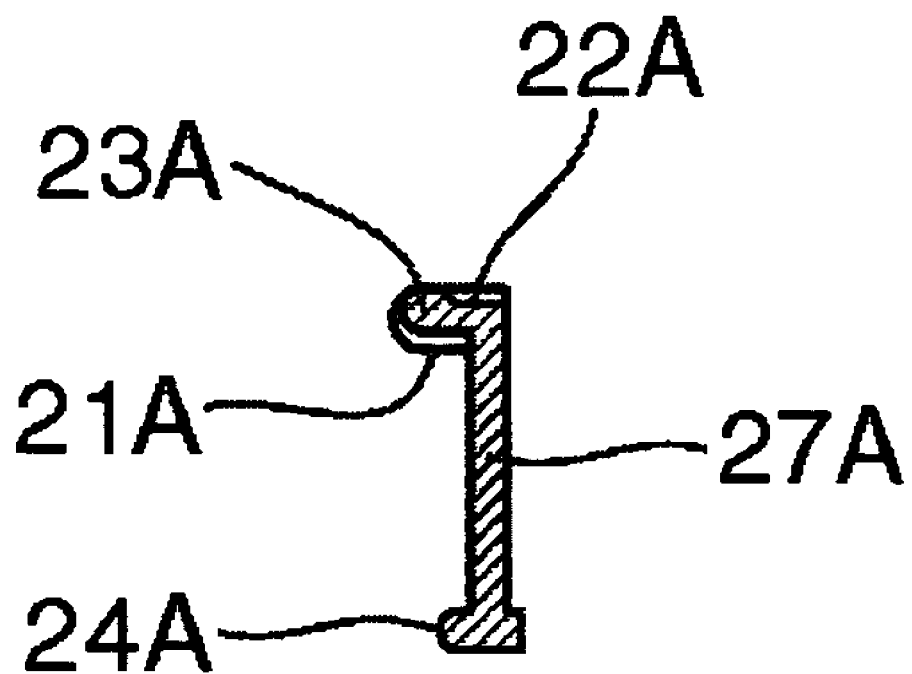
FIG. 6 is a sectional view taken along line VI—VI in FIG. 4.
Figure 7:
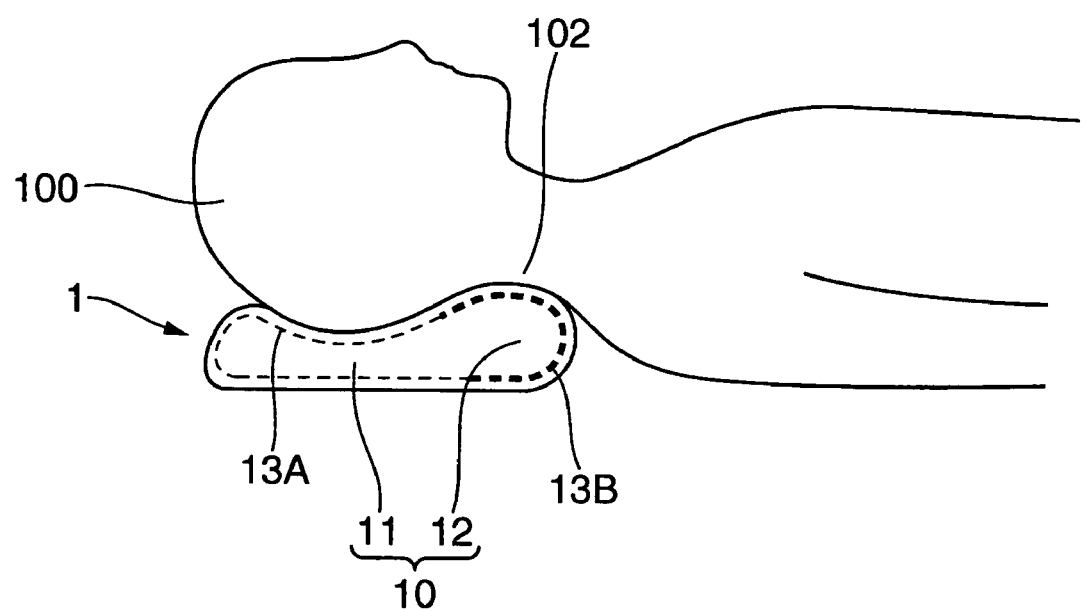
FIG. 7 shows the pillow in FIG. 1 in use.
Figure 8:
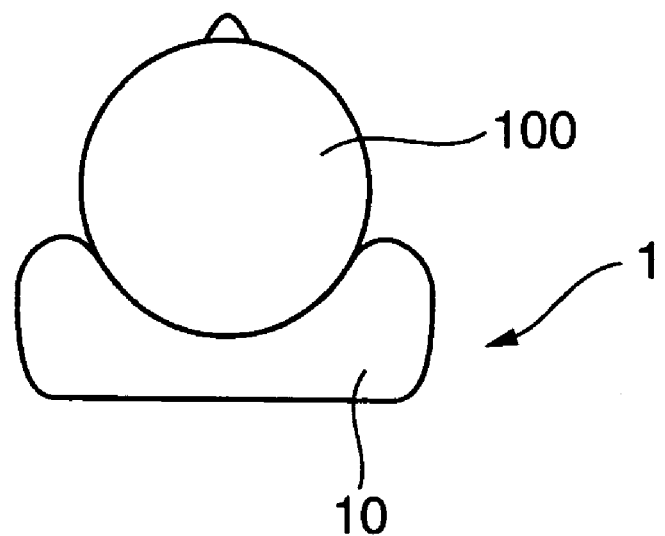
FIG. 8 shows the pillow in use in FIG. 7 as viewed from the top of the head of a user.

FIG. 1 is a perspective view of a pillow (partially omitted) according to an embodiment of this invention, some parts being cut away. FIG. 2 is a side view of the pillow in FIG. 1 (thick wefts indicated in black and thin wefts in white). FIG. 3 is a plan view of the pillow in FIG. 1 (partially omitted). FIG. 4 is a sectional view of a frame body taken along line II—II FIG. 1. FIG. 5 is a sectional view taken along line V—V in FIG. 4. FIG. 6 is a sectional view taken along line VI—VI in FIG. 4. FIG. 7 shows the pillow of FIG. 1 in use. FIG. 8 shows the pillow in FIG. 7 in use as viewed from the top of the head of the user.

In the explanation of this embodiment, a "longitudinal direction" refers to a direction extending from one side of the pillow to the other side.

As shown in FIGS. 1 to 8, the pillow 1 of this embodiment consists of a pillow body 10 having a head-supporting section 11 for supporting the head 100 of a user and a neck-supporting section 12 for supporting the neck 102 of the user, and frame bodies 20A and 20B disposed at the longitudinal sides of the pillow body 10 to support the same. The pillow body 10 is a woven article of resin-made long elements and is formed such that the neck-supporting section 12 is harder than the head-supporting section 11.

Specifically, the pillow body 10 comprises wefts 13A and 13B of different thicknesses extending from one frame body 20A to the other frame body 20B, and warps 14 extending at substantially right angles to the wefts 13A and 13B. The wefts 13B are made thicker than the wefts 13A. The wefts 13A (indicated in white in FIG. 2) are used in the head-supporting section 11 while the wefts 13B (indicated in black in FIG. 2) are used in the neck-supporting section 12.

More specifically, the wefts 13B are formed to have a cross section, substantially vertical to the longitudinal direction (extending from the frame body 20A to the opposite frame body 20B), larger than that of the wefts 13A. Because of the difference in thickness between the wefts 13A and 13B, the neck-supporting section 12 is formed to be harder than the head-supporting section 11.

In this embodiment, long elements made of nylon are used as the wefts 13A and 13B and the warps 14. These wefts 13A and 13B and warps 14 have crescent-shaped (arched) cross sections substantially vertical to the longitudinal direction. As described later, the pillow body 10 obtained by weaving these long elements looks beautiful as if it is made of real rattan.

The frame bodies 20A and 20B are formed separately from the pillow body 10. Because the frame bodies 20A and 20B are of the same shape, explanations are only given for the frame body 20A and explanations on the frame body 20B will be omitted since the reference letter A can be replaced with the reference letter B.

When viewed from above, the frame body 20A has a substantially oval shape with a central area being hollow. An outer frame 21A of the frame body 20A has concave grooves 22A where the wefts 13A and 13B are engaged and passed around, and small protrusions 23A of substantially the same width as the concave grooves 22A, these grooves and protrusions being alternately formed on the outer frame 21A. (See FIG. 4)

An inner frame 24A of the frame body 20A has a connecting portion 28A which is running through substantially the center of space 19 defined by the inner frame 24A and in the height direction of the pillow 1 (vertical direction in FIG. 4). At nearly the middle of the connecting portion 28A, a tubular member 26A is provided through which a substantially columnar supporting rod 25 is arranged approximately parallel to the longitudinal direction of the pillow 1. The supporting rod 25 is engaged into the tube-like members 26A and 26B to connect the frame bodies 20A and 20B and to enhance the strength of the pillow 1. The inner frame 24A also has, at its curved portions, fixing members 29A and 31A by which reinforcing members 30 made of longitudinal elements having semi-ring shaped cross sections are fixed. These fixing members 29A and 31A are complementary to the curved portions of the inner frame 24A and have engaging members 32A and 33A respectively for engaging the ends on one side of the reinforcing members 30. The other ends of the reinforcing members 30 are engaged respectively with the engaging members 32B and 33B formed in the fixing members 29B and 31B. These two reinforcing members 30 further enhance the strength of the pillow 1.

Between the outer frame 21A and the inner frame 24A of the frame body 20A, small rods 27A extend from every other small protrusion 23A to the inner frame 24A so that the outer frame 21A and the inner frame 24A are coupled. The frame body 20A is integrally molded with synthetic resin.

The head-supporting section 11 of the pillow body 10 is formed by engaging one end of the weft 13A into a concave groove 22A of the frame body 20A and passing it around behind a small rod 27A, then engaging the weft 13A into a concave groove 22B of the opposite frame body 20B and passing it around to the back of a small rod 27B, then skipping one small protrusion 23A and engaging it to another concave groove 22A next to the previous concave groove 22A to turn it around. This weaving process is repeatedly performed with the warp 14 to obtain the head-supporting section 11. Likewise, the neck-supporting section 12 is formed using the weft 13B. The frame body 20A prevents reversing of the front and back sides of the wefts 13A and 13B, accordingly, the wefts 13A and 13B and the warp 14 can be woven into the pillow body 10 in a beautiful finish.

It is preferable that the small protrusions 23A formed in the area of the head-supporting section 11 have about the same height and width as the weft 13A while the small protrusions 23A formed in the neck-supporting section 12 have about the same height and width as the weft 13B. With these settings of the small protrusions, although the wefts 13A and 13B are not passed around the inner frame 24A, the frame body looks as if the wefts 13A and 13B are passed around the inner frame 24A since the inner frame 24A is integrally coupled to the outer frame 21A with the small rods 27A, thus resulting in an aesthetically-pleasing look.

Since the frame body 20A is a molded article of synthetic resin and can be mass-produced, productivity is increased and the manufacturing costs can be reduced.

With regard to the pillow 1 manufactured as explained, the head-supporting section 11 for supporting the user's head is formed with the weft 13A and the neck-supporting section 12 for supporting the neck is formed with the weft 13B which is thicker than the weft 13A. Accordingly, how the pillow 1 sinks depends on the difference in weight between the head and the neck and the pillow reasonably conforms to the shape of the head and the neck as shown in FIGS. 7 and 8. Therefore, the pillow has an advantage that little stress is imposed on the head and the neck. Specifically, when the user lies on his back with his head on the pillow 1, the section formed with the thick weft 13B does not sink too much while the section formed with the thin weft 13A sinks to a considerable extent due to the weight of the head and takes on a concave shape to fit the head. Accordingly, the user can comfortably use the pillow with no stress imposed on his head and neck as in the case of using an urethane pillow.

In this embodiment, nylon yarn (long elements) were used for the wefts 13A and 13B and the warp 14. The pillow 1 made from nylon resin has characteristics that it softens due to the heat of the user's head and the neck and conforms naturally to the shape of the head and the neck, hence enhancing the user's comfort. Moreover, nylon resin is able to absorb about 10% of the moisture and is effective in lowering the temperature of the head and the neck about two to three degrees by absorbing the heat thereof, thus providing a further enhanced comfort to the user. The pillow is also good for one's health since it creates a state where the user's head is cool and the feet are warm.

By using different colors for the weft 13A constituting the head-supporting section 11 and the weft 13B constituting the neck-supporting section 12, the user can easily notice the orientation of the pillow 1 and the usability of the pillow 1 is enhanced.

Although the wefts of different thicknesses were used in this embodiment to make a difference in hardness between the head-supporting section 11 and the neck-supporting section 12, without limitation to the above, any means can be applied to make the head-supporting section 11 and the neck-supporting section 12 have different thicknesses, such as using wefts of different hardness or changing the thickness of the warp.

In this embodiment, explanations were given for the case in which the pillow body 10 is formed by weaving the wefts 13A and 13B and the warp 14 while passing the wefts 13A and 13B around the frame bodies 20A and 20B. This invention, however, is not limited to this embodiment. The pillow body 10 can be solely formed in advance by weaving the wefts 13A and 13B and the warp 14, and then, it is attached to the frame bodies 20A and 20B.

In this case, the frame bodies 20A and 20B may be attached to the pillow body 10 so that the pillow body 10 will be in a tubular form. It is also possible not to attach both ends (substantially vertical to the longitudinal direction of the pillow body 10) of the pillow body 10 (i.e., the pillow will not be in a tubular form) so that there is a space between the ends.

Figure 9:
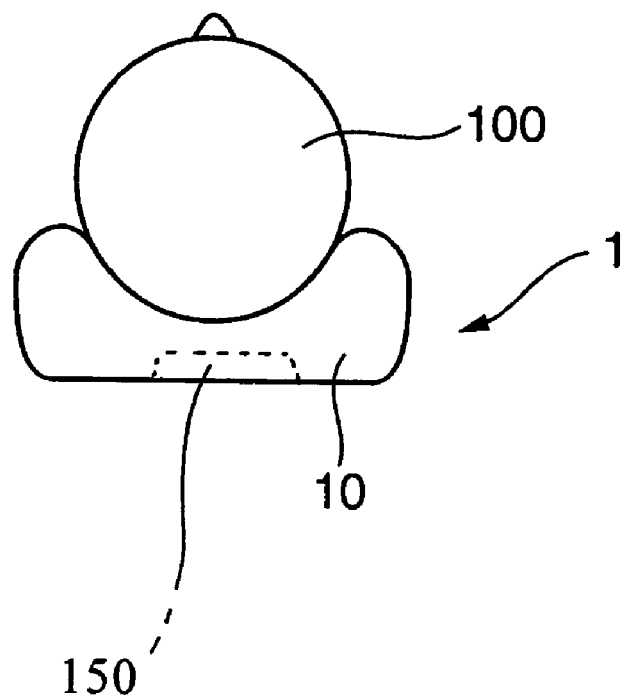
FIG. 9 is a schematic view showing that an optional article is arranged in a space formed by the frame bodies and the pillow body of the pillow in FIG. 1.

The pillow 1 according to this invention allows a desired article 150 to be optionally arranged in a space formed by the pillow body 10 and the frame bodies 20A and 20B as shown in FIG. 9. Examples of the desired article 150 include fragrant materials, audio-generating devices and herbs but there are no particular limitations.

As shown in FIGS. 10 (A) and (B), the head-supporting section of the pillow 1 of this invention starts to sink gradually and naturally right after the user lays down (indicated by wavy lines in the figures) due to the weight of the head. Accordingly, the head is kept at a low position while the neck remains in the same position (indicated by solid lines in FIGS. 10(A) and (B)). Therefore, compared to using other pillows, the pillow 1 of this invention provides a better condition for the respiratory organs and expands the respiratory airway, thus preventing snoring. This pillow can be preferably used by people with apnea syndrome. Moreover, the pillow is effective in solving insomnia and promoting one's health by guaranteeing excellent comfort while sleeping.

The pillow of this invention may be provided with a pillow case if desired. For example, during a very cold time in the winter, the pillow may be covered with a pillow case which is made from a material having a certain degree of thermal insulating function to maintain a comfortable temperature.

As explained, the pillow of this invention is a woven article of long resin-made elements and has an appropriate height, resiliency, and hardness since the neck-supporting section is made harder than the head-supporting section, hence the user will not suffer from too much stress on the head and the neck region. Moreover, the pillow can enhance air permeability and heat dispersion and is lightweight and excellent in strength.

I claim:

1. A pillow comprising:
   a pair of frame bodies oppositely disposed and spaced apart from each other; and
   a pillow body disposed to surround the peripheries of the frame bodies,
   wherein the pillow body is a woven article of long elements and has a head-supporting section for supporting a user's head and a neck-supporting section for supporting the user's neck, and the neck-supporting section is harder than the head-supporting section.

2. A pillow according to claim 1 wherein a main component of the long element is resin.

3. A pillow according to claim 1 wherein,
   the woven article comprises a weft extending from one of the body frame to the other body frame and a warp extending in an substantially vertical direction to the weft, and
   the weft arranged in the neck-supporting section has a cross section, which is in a vertical direction in relation to the longitudinal direction of the weft, larger than that of the weft arranged in the head-supporting section.

4. A pillow according to claim 3 wherein the color of the weft arranged in the neck-supporting section is different from that of the weft arranged in the head-supporting section.

5. A pillow according to claim 1 wherein,
the woven article comprises a weft extending from one of the body frames to the other body frame and a warp extending in a substantially vertical direction to the weft, and
the weft arranged in the neck-supporting section is harder than the weft arranged in the head-supporting section.

6. A pillow according to claim 5 wherein at least either one of the warps and the wefts has a cross section in a substantially crescent shape, substantially vertical to the longitudinal direction thereof.

7. A pillow according to claim 1 wherein a main component of the long element is nylon resin.

8. A pillow according to claim 1 wherein each of the frame bodies, in a plan view, has a substantially oval shape and has reinforcing members at its curved portions.

9. A pillow according to claim 1 wherein one of the frame bodies is coupled to the other frame body by a supporting rod.

10. A pillow according to claim 1 wherein an article is arranged in a space formed by the frame bodies and the pillow body.

11. A pillow according to claim 10 wherein the optional article is at least one from among a fragrant material, audio-generating device and herb.

* * * * *